(12) United States Patent
Aizawa et al.

(10) Patent No.: US 9,695,124 B2
(45) Date of Patent: Jul. 4, 2017

(54) METHOD OF PRODUCING 2-AMINONICOTINIC ACID BENZYL ESTER DERIVATIVES

(71) Applicant: AGRO-KANESHO CO., LTD., Minato-ku (JP)

(72) Inventors: Ryo Aizawa, Tokorozawa (JP); Itaru Okada, Sagamihara (JP)

(73) Assignee: AGRO-KANESHO CO., LTD., Minato-ku (JP)

( * ) Notice: Subject to any disclaimer, the term of this patent is extended or adjusted under 35 U.S.C. 154(b) by 0 days.

(21) Appl. No.: 15/107,649

(22) PCT Filed: Dec. 27, 2013

(86) PCT No.: PCT/JP2013/085073
§ 371 (c)(1),
(2) Date: Jun. 23, 2016

(87) PCT Pub. No.: WO2015/097850
PCT Pub. Date: Jul. 2, 2015

(65) Prior Publication Data
US 2016/0318868 A1    Nov. 3, 2016

(51) Int. Cl.
*C07D 213/803* (2006.01)
*C07D 401/12* (2006.01)

(52) U.S. Cl.
CPC ....... *C07D 213/803* (2013.01); *C07D 401/12* (2013.01)

(58) Field of Classification Search
CPC .................................................. C07D 213/803
USPC ................................................. 546/264, 310
See application file for complete search history.

(56) References Cited

U.S. PATENT DOCUMENTS

| | | |
|---|---|---|
| 4,895,950 A | 1/1990 | Lindel et al. |
| 4,948,421 A | 8/1990 | Someya et al. |
| 5,207,819 A | 5/1993 | Someya et al. |
| 2011/0009454 A1 | 1/2011 | Matsuzaki et al. |

FOREIGN PATENT DOCUMENTS

| | | |
|---|---|---|
| JP | 63-264583 A | 11/1988 |
| JP | 64-31768 A | 2/1989 |
| JP | 2010-83861 A | 4/2010 |
| WO | 2014/006945 A1 | 1/2014 |

OTHER PUBLICATIONS

International Search Report issued Apr. 1, 2014 in PCT/JP2013/085073 filed on Dec. 27, 2013.
Sergio H. Szajnman, et al., "Design and Synthesis of Aryloxyethyl Thiocyanate Derivatives as Potent Inhibitors of *Trypanosoma cruzi* Proliferation", Journal of Medicinal Chemistry, vol. 43, No. 9, 2000, pp. 1826-1840.

*Primary Examiner* — Patricia L Morris
(74) *Attorney, Agent, or Firm* — Oblon, McClelland, Maier & Neustadt, L.L.P.

(57) ABSTRACT

The present invention provides a method of producing a 2-aminonicotinic acid benzyl ester derivative at a high yield and with a high purity. By reacting a benzyl halide derivative with a 2-aminonicotinic acid derivative in a polar solvent in the presence of a prescribed base, it is possible to obtain a 2-aminonicotinic acid benzyl ester derivative at a high yield and with a high purity.

12 Claims, No Drawings

METHOD OF PRODUCING 2-AMINONICOTINIC ACID BENZYL ESTER DERIVATIVES

TECHNICAL FIELD

The present invention relates to a method of producing a 2-aminonicotinic acid benzyl ester derivative. Specifically, the present invention relates to a method of producing a 2-aminonicotinic acid benzyl ester derivative, which is a compound useful as an active component of an agricultural fungicide, at a high yield and with a high purity.

BACKGROUND ART

Examples of the method of producing a 2-aminonicotinic acid ester derivative include a method comprising chlorination of a 2-aminonicotinic acid derivative with a halogenating agent and a reaction of the chlorinated product with a benzyl alcohol derivative in the presence of a base in an organic solvent and a method comprising a reaction between a 2-aminonicotinic acid derivative and a benzyl alcohol derivative using a condensing agent in an organic solvent.

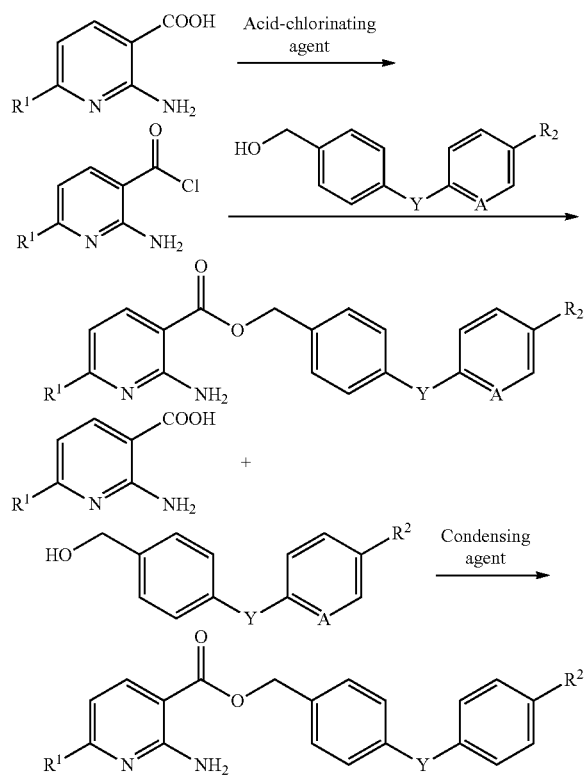

SUMMARY OF INVENTION

In the conventional technologies, the yield is low, and purification by, for example, silica gel column chromatography, is necessary for removing the remaining unreacted raw material, 2-aminonicotinic acid derivative. It has been accordingly demanded to develop a method for industrially producing a target product at a high yield and with a high purity.

The present inventors have diligently studied to solve the above-mentioned problems and, as a result, have found that chlorination of a 2-aminonicotinic acid derivative makes a reaction solution turn dark brown, prevents the target reaction from progressing, and increases an amount of by-products. In addition, it has been revealed that the reaction is not completed even if a condensing agent is used. Therefore, production of a 2-aminonicotinic acid benzyl ester derivative by the conventional technologies needs a purification process and has a low yield.

The present inventors also found that a 2-aminonicotinic acid benzyl ester derivative can be prepared at a high yield and with a high purity by reacting a benzyl halide derivative with a 2-aminonicotinic acid derivative in the presence of a prescribed base in a polar solvent, and arrived at the present invention.

That is, an aspect of the present invention provides a method of producing a 2-aminonicotinic acid benzyl ester derivative represented by the following Formula [I]:

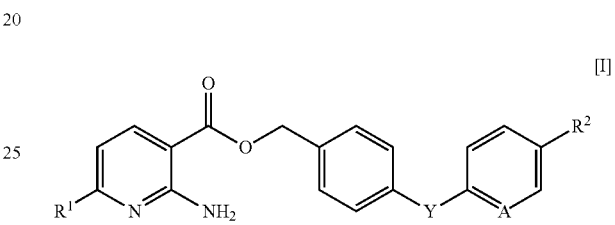

wherein $R^2$ represents a hydrogen atom or a $C_1$-$C_4$ alkyl group; $R^2$ represents a hydrogen atom, a halogen atom, a $C_1$-$C_4$ alkyl group, or a $C_1$-$C_4$ alkoxy group; A represents a nitrogen atom or a methine group (CH); and Y represents an oxygen atom, a methylene group ($CH_2$), or a methyleneoxy group ($OCH_2$), the method comprising:

(a) reacting a 2-aminonicotinic acid derivative represented by the following Formula [II]:

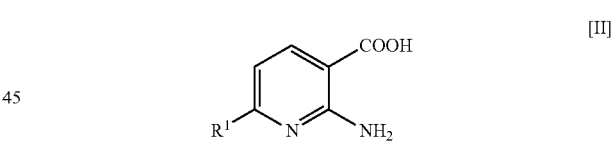

wherein $R^2$ is the same as that defined in Formula [I], with an alkali metal hydride or an alkali metal carbonate to prepare a compound represented by the following Formula [III]:

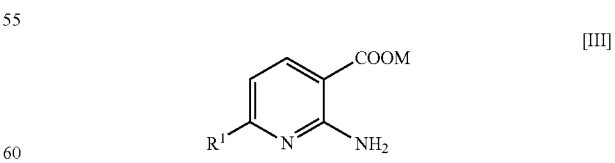

wherein $R^1$ is the same as that defined in Formula [I], and M represents an alkali metal; and (b) reacting the compound represented by Formula [III] prepared in the step (a) with a benzyl halide derivative represented by the following Formula [IV]:

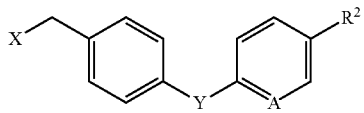

wherein $R^2$, A, and Y are the same as those defined in Formula [I], and X represents a halogen atom,
in a polar solvent to produce the 2-aminonicotinic acid benzyl ester derivative represented by Formula [I].

Another aspect of the present invention provides a method of producing a 2-aminonicotinic acid benzyl ester derivative represented by the following Formula [I]:

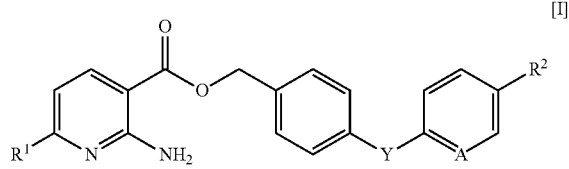

wherein $R^1$ represents a hydrogen atom or a $C_1$-$C_4$ alkyl group; $R^2$ represents a hydrogen atom, a halogen atom, a $C_1$-$C_4$ alkyl group, or a $C_1$-$C_4$ alkoxy group; A represents a nitrogen atom or a methine group (CH); Y represents an oxygen atom, a methylene group ($CH_2$), or a methyleneoxy group ($OCH_2$),
the method comprising:
(a) reacting a 2-aminonicotinic acid derivative represented by the following Formula [II]:

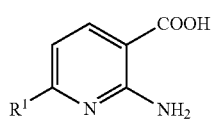

wherein $R^1$ is the same as that defined in Formula [I], with an alkali metal hydride or an alkali metal carbonate to prepare a compound represented by the following Formula [III]:

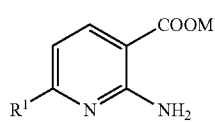

wherein $R^1$ is the same as that defined in Formula [I], and M represents an alkali metal;
(b) reacting a benzyl alcohol derivative represented by the following Formula [V]:

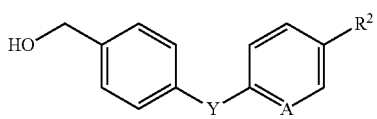

wherein $R^2$, A, and Y are the same as those defined in Formula [I],
with a halogenating agent to prepare a benzyl halide derivative represented by the following Formula [IV]:

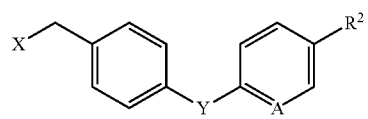

wherein $R^2$, A, and Y are the same as those defined in Formula [I], and X represents a halogen atom; and
(c) reacting the benzyl halide derivative represented by Formula [IV] prepared in the step (b), without being isolated, with the compound represented by Formula [III] prepared in the step (a) in a polar solvent to produce the 2-aminonicotinic acid benzyl ester derivative represented by Formula [I].

The production methods of the present invention can produce a 2-aminonicotinic acid benzyl ester derivative with a higher purity and a higher yield compared to the conventional methods.

DESCRIPTION OF EMBODIMENTS

The present invention will now be described in detail.
In Formulae [I], [II], [III], [IV], and [V], examples of the $C_1$-$C_4$ alkyl group represented by $R^1$ or $R^2$ include methyl, ethyl, n-propyl, isopropyl, n-butyl, isobutyl, sec-butyl, and tert-butyl groups; examples of the halogen atom represented by $R^2$ include fluorine, chlorine, bromine, and iodine atoms; examples of the $C_1$-$C_4$ alkoxy group represented by $R^2$ include methoxy, ethoxy, n-propoxy, isopropoxy, n-butoxy, isobutoxy, sec-butoxy, and tert-butoxy groups; and examples of the alkali metal represented by M include lithium, sodium, potassium, and cesium.

In an embodiment of the present invention, the production method can include steps of adding a compound of Formula [II] to a polar solvent, such as N,N-dimethylformamide, N,N-dimethylacetamide, N-methylpyrrolidone, 1,3-dimethyl-2-imidazolidinone, acetonitrile, or dimethyl sulfoxide, further adding a base, such as sodium carbonate, potassium carbonate, or cesium carbonate, to the polar solvent in an amount of 1.0 to 3.0 times by mole, preferably 1.5 to 2.0 times by mole, relative to an amount of the compound of Formula [II], and stirring the mixture at a temperature of 0° C. to 60° C. for 5 minutes to 2 hours, preferably at a temperature of 30° C. to 50° C. for 10 to 30 minutes, to prepare a suspension (hereinafter, referred to as Suspension 1) of the compound of Formula [III]. The method can also include steps of adding a compound of Formula [V] to a polar solvent, such as N,N-dimethylformamide, N,N-dimethylacetamide, N-methylpyrrolidone, 1,3-dimethyl-2-imidazolidinone, acetonitrile, or dimethyl sulfoxide, further adding a halogenating agent, such as thionyl chloride, thionyl bromide, or phosphorus oxychloride, to the polar solvent in an amount of 1.0 to 1.5 times by mole, preferably 1.0 to 1.1 times by mole, relative to an amount of the compound of Formula [V], and stirring the mixture at a temperature of −5° C. to 30° C. for 5 minutes to 1 hour, preferably at a temperature of 0° C. to 10° C. for 20 to 40 minutes, to prepare a solution of the compound of Formula [IV]. The method can also include a step of dropwise adding the resulting solution to Suspension 1, and stirring the mixture with heating at a temperature of 0° C. to 100° C. for 1 to 20 hours, preferably at a temperature of 60° C. to 80° C. for 2 to 16 hours, for a reaction to produce a compound of Formula [I]. After the reaction, the reaction solution may be distilled under reduced pressure to remove 50% to 95% of the organic solvent, iced water may be poured into the solution, and the mixture may be stirred for 5 to 30 minutes, preferably to 20 minutes, to precipitate crystals, followed by collection of the crystals by filtration. The collected crystals may be washed with water and then dried. Thus, the target compound of Formula [I] can be significantly easily prepared at a high yield and with a high purity.

In another embodiment, the production method of the present invention can include steps of adding a compound of Formula [II] to a polar solvent, such as N,N-dimethylformamide, N,N-dimethylacetamide, N-methylpyrrolidone, 1,3-dimethyl-2-imidazolidinone, acetonitrile, or dimethyl sulfoxide, further adding a base, such as sodium carbonate, potassium carbonate, or cesium carbonate, to the polar solvent in an amount of 1.0 to 3.0 times by mole, preferably 1.5 to 2.0 times by mole, relative to an amount of the compound of Formula [II], stirring the mixture at a temperature of 0° C. to 60° C. for 5 minutes to 2 hours, preferably at a temperature of 30° C. to 50° C. for 10 to 30 minutes to prepare a suspension, and then dropwise adding a compound of Formula [IV] to the suspension, and stirring the mixture with heating at a temperature of 0° C. to 100° C. for 1 to 20 hours, preferably at a temperature of 60° C. to 80° C. for 2 to 16 hours, for a reaction to produce a compound of Formula [I]. After the reaction, the reaction solution may be distilled under reduced pressure to remove 50% to 95% of the organic solvent, iced water may be poured into the reaction solution and the mixture may be stirred for 5 to 30 minutes, preferably 10 to 20 minutes, to precipitate crystals, followed by collection of the crystals by filtration. The collected crystals may be washed with water and then dried. Thus, the target compound of Formula [I] can be significantly easily prepared at a high yield and with a high purity.

In the production method of the present invention, an alkali metal hydride that reacts with a compound of formula [II] is not particularly limited, but includes lithium hydride, sodium hydride, potassium hydride, and cesium hydride.

In the production method of the present invention, an alkali metal carbonate that reacts with a compound of Formula [II] is not particularly limited, but includes sodium carbonate, potassium carbonate, and cesium carbonate.

In the production method of the present invention, an amount of the alkali metal hydride or the alkali metal carbonate that reacts with a compound of Formula [II] is not particularly limited, but is, for example, 1.0 to 3.0 times by mole, preferably 1.5 to 2.0 times by mole, relative to an amount of the compound of Formula [II].

In the production method of the present invention, the reaction of a compound of Formula [II] with an alkali metal hydride or an alkali metal carbonate is not particularly limited, but is performed by, for example, stirring them in a polar solvent, such as N,N-dimethylformamide, N,N-dimethylacetamide, N-methylpyrrolidone, 1,3-dimethyl-2-imidazolidinone, acetonitrile, or dimethyl sulfoxide, for example, at a temperature of 0° C. to 60° C. for 5 minutes to 2 hours, preferably at a temperature of 30° C. to 50° C. for 10 to 30 minutes.

In the production method of the present invention, the reaction between a compound of Formula [III] and a compound of Formula [IV] is not particularly limited, but is performed by, for example, dropwise adding a solution of a compound of Formula [IV] to a suspension of a compound of Formula [III], and stirring the mixture with heating, for example, at a temperature of 0° C. to 100° C. for 1 to 20 hours, preferably at a temperature of 60° C. to 80° C. for 2 to 16 hours.

In the production method of the present invention, the halogenating agent that reacts with a compound of Formula [V] is not particularly limited, but includes thionyl chloride, thionyl bromide, or phosphorus oxychloride. The halogenating agent is used in an amount of, for example, 1.0 to 1.5 times by mole, preferably 1.0 to 1.1 times by mole, relative to the amount of the compound of Formula [V].

In the production method of the present invention, the reaction between a compound of Formula [V] and a halogenating agent is not particularly limited, but is performed, for example, in a polar solvent, such as N,N-dimethylformamide, N,N-dimethylacetamide, N-methylpyrrolidone, 1,3-dimethyl-2-imidazolidinone, acetonitrile, or dimethyl sulfoxide, for example, at a temperature of −5° C. to 30° C. for 5 minutes to 1 hour, preferably at a temperature of 0° C. to 10° C. for 20 to 40 minutes.

In the production method of the present invention, the compound of Formula [IV] produced by a reaction between a compound of Formula [V] and a halogenating agent can react, without being isolated, with a compound of Formula [III].

In the production method of the present invention, the polar solvent that is used in the reaction between a compound of Formula [II] and an alkali metal hydride or alkali metal carbonate may be the same as or different from the polar solvent that is used in the reaction between a compound of Formula [V] and a halogenating agent, preferably, they are the same.

The nicotinic acid derivative represented by Formula [II] to be used in the production method of the present invention can be instantly synthesized from known compounds in accordance with, for example, the method described in JP-A-2010-083861.

The alcohol derivative represented by Formula [V] to be used in the production method of the present invention can be instantly synthesized from known compounds in accordance with, for example, the method described in Journal of Medicinal Chemistry, Vol. 43, p. 1826 (2000).

The compound of Formula [I] produced by the production method of the present invention is useful as an agricultural fungicide.

EXAMPLES

The present invention will now be further described by Examples, but the scope of the present invention is not limited to the following Examples.

Example 1

Synthesis of 2-amino-6-methyl nicotinic acid-4-phenoxybenzyl

4-Phenoxybenzyl alcohol (4.00 g) was dissolved in N,N-dimethylformamide (10 mL), and the solution was cooled to 5° C. Thionyl chloride (1.45 mL) was dropwise added to this solution, and the mixture was then stirred for 30 minutes to prepare solution (I).

2-Amino-6-methyl nicotinic acid (3.04 g) was suspended in N,N-dimethylformamide (60 mL). Potassium carbonate (5.53 g) was added to the suspension, followed by stirring at 40° C. for 30 minutes. Solution (I) was dropwise added to the resulting suspension, followed by stirring with heating at 80° C. for 2 hours. The reaction solution was cooled to room temperature, and the N,N-dimethylformamide (40 mL, 57%) was removed by distillation under reduced pressure. Iced water (100 mL) was added to the residue, followed by stirring at room temperature for minutes. Precipitated crystals were collected by filtration and were dried to give 6.41 g (yield: 96%) of the target product (Compound 2 shown in Table 1). According to purity analysis by liquid chromatography, the purity of thus obtained target product was high, 99.6%. A melting point thereof was 122° C. to 124° C.

$^1$H-NMR (CDCl$_3$) δppm: 2.38 (3H, s), 5.25 (2H, s), 6.06-6.72 (2H.br), 6.44 (1H, d), 6.99-7.04 (4H, m), 7.12 (1H, t), 7.31-7.41 (4H, m), 8.04 (1H, d)

Example 2

Synthesis of 2-amino-6-methyl nicotinic acid-4-phenoxybenzyl

4-Phenoxybenzyl alcohol (4.00 g) was dissolved in acetonitrile (10 mL), and the solution was cooled to 5° C. Thionyl chloride (1.45 mL) was dropwise added to this solution, and the mixture was then stirred for 30 minutes to prepare solution (I).

2-Amino-6-methyl nicotinic acid (3.04 g) was suspended in acetonitrile (50 mL), and potassium carbonate (5.53 g) was added to the suspension, followed by stirring at 40° C. for 30 minutes. Solution (I) was dropwise added to the resulting suspension, followed by reflux for 16 hours. The reaction solution was cooled to room temperature and was concentrated under reduced pressure. Iced water (200 mL) was added to the residue, followed by stirring at room temperature for 10 minutes. Precipitated crystals were collected by filtration and were dried to give 6.05 g (yield: 91%) of the target product (Compound 2 shown in Table 1). According to purity analysis by liquid chromatography, the purity of thus obtained target product was high, 98.9%. A melting point thereof was 122° C. to 124° C.

$^1$-NMR (CDCl$_3$) δppm: 2.38 (3H, s), 5.25 (2H, s), 6.06-6.72 (2H.br), 6.44 (1H, d), 6.99-7.04 (4H, m), 7.12 (1H, t), 7.31-7.41 (4H, m), 8.04 (1H, d)

Example 3

Synthesis of 2-amino-6-methyl nicotinic acid-4-phenoxybenzyl

2-Amino-6-methyl nicotinic acid (3.04 g) was suspended in N,N-dimethylformamide (60 mL), and potassium carbonate (5.53 g) was added to the suspension, followed by stirring at 40° C. for 30 minutes. 4-Phenoxybenzyl chloride (4.37 g) was dropwise added to the resulting suspension, followed by stirring with heating at 80° C. for 2 hours. The reaction solution was cooled to room temperature, and the N,N-dimethylformamide (35 mL, 58%) was removed by distillation under reduced pressure. Iced water (100 mL) was added to the residue, followed by stirring at room temperature for 10 minutes. Precipitated crystals were collected by filtration and were dried to give 6.42 g (yield: 96%) of the target product (Compound 2 shown in Table 1). According to purity analysis by liquid chromatography, the purity of thus obtained target product was high, 99.7%. A melting point thereof was 122° C. to 124° C.

$^1$H-NMR (CDCl$_3$) δppm: 2.38 (3H, s), 5.25 (2H, s), 6.06-6.72 (2H.br), 6.44 (1H, d), 6.99-7.04 (4H, m), 7.12 (1H, t), 7.31-7.41 (4H, m), 8.04 (1H, d)

Reference Example 1

The 4-phenoxybenzyl chloride used in Example 3 was synthesized by the following process.

Synthesis of 4-phenoxybenzyl chloride

4-Phenoxybenzyl alcohol (20.0 g) was dissolved in toluene (100 mL), and thionyl chloride (13.1 g) was added to the solution over 30 minutes at room temperature. After 2 hours, the reaction solution was concentrated under reduced pressure. The residue was distilled to give 16.7 g (yield: 76%) of the target product. A boiling point thereof was 137° C./3 mmHg.

Example 4

Synthesis of 2-amino-6-methyl nicotinic acid-4-(4-methylphenoxy)benzyl 4-(4-Methylphenoxy)benzyl alcohol (4.26 g) was dissolved in N,N-dimethylformamide (10 mL), and the solution was cooled to 5° C. Thionyl chloride (1.45 mL) was dropwise added to this solution, and the mixture was then stirred for 30 minutes to prepare solution (I).

2-Amino-6-methyl nicotinic acid (3.04 g) was suspended in N,N-dimethylformamide (60 mL), and potassium carbonate (5.53 g) was added to the suspension, followed by stirring at 40° C. for 30 minutes. Solution (I) was dropwise added to the resulting suspension, followed by stirring with heating at 80° C. for 2 hours. The reaction solution was cooled to room temperature, and the N,N-dimethylformamide (45 mL, 64%) was removed by distillation under reduced pressure. Iced water (100 mL) was added to the residue, followed by stirring at room temperature for minutes. Precipitated crystals were collected by filtration and were dried to give 6.42 g (yield: 92%) of the target product (Compound 4 shown in Table 1). According to purity analysis by liquid chromatography, the purity of thus obtained target product was high, 99.1%. A melting point thereof was 94° C. to 96° C.

$^1$H-NMR (CDCl$_3$) δppm: 2.33 (3H, s), 2.40 (3H, s), 5.27 (2H, s), 6.08-6.82 (2H, br), 6.44 (1H, d), 6.90-7.00 (5H, m), 7.14 (2H, d), 7.37 (2H, d), 8.02 (1H, d)

Example 5

Synthesis of 2-amino-6-methyl nicotinic acid-4-phenylmethyl benzyl

4-Phenylmethyl benzyl alcohol (3.96 g) was dissolved in N,N-dimethylformamide (10 mL), and the solution was cooled to 5° C. Thionyl chloride (1.45 mL) was dropwise added to this solution, and the mixture was then stirred for 30 minutes to prepare solution (I).

2-Amino-6-methyl nicotinic acid (3.04 g) was suspended in N,N-dimethylformamide (60 mL), and potassium carbonate (5.53 g) was added to the suspension, followed by stirring at 40° C. for 30 minutes. Solution (I) was dropwise added to the resulting suspension, followed by stirring with heating at 80° C. for 2 hours. The reaction solution was cooled to room temperature, and the N,N-dimethylformamide (40 mL, 57%) was removed by distillation under reduced pressure. Iced water (100 mL) was added to the residue, followed by stirring at room temperature for minutes. Precipitated crystals were collected by filtration and were dried to give 6.08 g (yield: 91%) of the target product (Compound 8 shown in Table 1). According to purity analysis by liquid chromatography, the purity of thus obtained target product was high, 98.3%. A melting point thereof was 106° C. to 108° C.

$^1$H-NMR (CDCl$_3$) δppm: 2.40 (3H, s), 3.99 (2H, s), 5.25 (2H, s), 6.10-6.74 (2H, br), 6.43 (1H, d), 7.16-7.22 (4H, m), 7.24-7.34 (5H, m), 8.02 (1H, d)

Example 6

Synthesis of 2-amino-6-methyl nicotinic acid-4-(2-pyridyloxy)benzyl 4-(2-Pyridyloxy)benzyl alcohol (4.02 g) was dissolved in N,N-dimethylformamide (10 mL), and the solution was cooled to 5° C. Thionyl chloride (1.45 mL) was dropwise added to this solution, and the mixture was then stirred for 30 minutes to prepare solution (I).

2-Amino-6-methyl nicotinic acid (3.04 g) was suspended in N,N-dimethylformamide (60 mL), and potassium carbonate (5.53 g) was added to the suspension, followed by stirring at 40° C. for 30 minutes. Solution (I) was dropwise added to the resulting suspension, followed by stirring with heating at 80° C. for 2 hours. The reaction solution was cooled to room temperature, and the N,N-dimethylformamide (50 mL, 71%) was removed by distillation under reduced pressure. Iced water (100 mL) was added to the residue, followed by stirring at room temperature for minutes. Precipitated crystals were collected by filtration and were dried to give 6.13 g (yield: 91%) of the target product (Compound 6 shown in Table 1). According to purity analysis by liquid chromatography, the purity of thus obtained target product was high, 98.5%. A melting point thereof was 120° C. to 121° C.

$^1$H-NMR (CDCl$_3$) δppm: 2.40 (3H, s), 5.31 (2H, s), 6.10-6.91 (2H, br), 6.46 (1H, d), 6.89 (1H, d), 7.00 (1H, t), 7.16 (2H, d), 7.43 (2H, d), 7.67-7.72 (1H, t), 8.03 (1H, d), 8.20 (1H, d)

Comparative Example 1

Synthesis of 2-amino-6-methyl nicotinic acid-4-phenoxybenzyl

2-Amino-6-methyl nicotinic acid (3.04 g) and thionyl chloride (15 mL) were mixed and stirred with heating at 85° C. for 1 hour. The target acid chloride was partially decomposed and made the reaction solution turn brown. An excess amount of the thionyl chloride was removed by distillation from the reaction solution. The residue was cooled to room temperature, and tetrahydrofuran (30 mL), 4-phenoxybenzyl alcohol (4.00 g), and triethylamine (6.06 g) were added to the residue. The mixture was stirred at room temperature for 1 hour, and water (80 mL) was added thereto. Insoluble matters were removed by filtration, and the filtrate was subjected to liquid separation. The organic layer was washed with saturated saline, dried with anhydrous sodium sulfate, and concentrated under reduced pressure. The residue was purified by silica gel column chromatography (hexane:ethyl acetate=2:1) to give 1.23 g (yield: 18%) of the target product. A melting point thereof was 122° C. to 124° C.

Comparative Example 2

Synthesis of 2-amino-6-methyl nicotinic acid-4-phenoxybenzyl

2-Amino-6-methyl nicotinic acid (3.04 g) was suspended in methylene chloride (100 mL), and the suspension was cooled to 5° C. Oxalyl chloride (2.58 mL) and N,N-dimethylformamide (several drops) were added to this suspension, followed by stirring for 2 hours to prepare solution (I). 4-Phenoxybenzyl alcohol (4.00 g) was dissolved in methylene chloride (100 mL), and 4-dimethylaminopyridine (3.36 g) was added thereto. The resulting solution was cooled to 5° C., and solution (I) was dropwise added thereto, followed by stirring for 1 hour. Water (200 mL) was added to the reaction solution, followed by being subjected to liquid separation. The organic layer was washed with saturated saline, dried with anhydrous sodium sulfate, and concentrated under reduced pressure. The residue was purified by silica gel column chromatography (hexane:ethyl acetate=2:1) to give 2.47 g (yield: 37%) of the target product. A melting point thereof was 122° C. to 124° C.

Comparative Example 3

Synthesis of 2-amino-6-methyl nicotinic acid-4-phenoxybenzyl

2-Amino-6-methyl nicotinic acid (3.04 g) was suspended in 1,2-dichloroethane (50 mL). 4-Phenoxybenzyl alcohol (4.00 g), 1-ethyl-3-(3-dimethylaminopropyl)carbodiimide (4.60 g), and 4-dimethylaminopyridine (2.92 g) were added to the suspension, followed by stirring with heating at 70° C. for hours. The reaction solution was cooled to room temperature and subjected to liquid separation using 1,2-dichloroethane (100 mL) and water (150 mL). The organic layer was washed with saturated saline, dried with anhydrous sodium sulfate, and concentrated under reduced pressure. The residue was purified by silica gel column chromatography (gradient of hexane/ethyl acetate) to give 3.87 g (yield: 58%) of the target product. A melting point thereof was 121° C. to 123° C.

Compounds of the present invention which were produced according to similar methods to the method of Example 1 are shown below.

TABLE 1

[IV]

| Compound No. | R$^1$ | R$^2$ | A | Y | mp (° C.) | Yield (%) | Purity (%) |
|---|---|---|---|---|---|---|---|
| 1 | H | H | CH | O | 116-118 | 94 | 99.1 |
| 2 | CH$_3$ | H | CH | O | 122-124 | 96 | 99.6 |
| 3 | CH$_3$ | F | CH | O | 104-106 | 93 | 98.9 |
| 4 | CH$_3$ | CH$_3$ | CH | O | 94-96 | 92 | 99.1 |
| 5 | CH$_3$ | OCH$_3$ | CH | O | 107-109 | 94 | 99.2 |
| 6 | CH$_3$ | H | N | O | 120-121 | 91 | 98.5 |
| 7 | CH$_3$ | H | CH | OCH$_2$ | 140-142 | 96 | 99.4 |
| 8 | CH$_3$ | H | CH | CH$_2$ | 106-108 | 91 | 98.3 |

As described above, the production method of the present invention is an industrially valuable method of producing an agricultural fungicide i.e. 2-aminonicotinic acid benzyl ester derivative.

The invention claimed is:

1. A method of producing a 2-aminonicotinic acid benzyl ester derivative represented by Formula [I]:

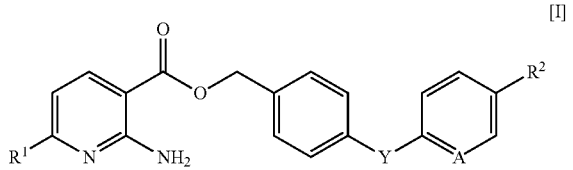

wherein $R^1$ represents a hydrogen atom or a $C_1$-$C_4$ alkyl group; $R^2$ represents a hydrogen atom, a halogen atom, a $C_1$-$C_4$ alkyl group, or a $C_1$-$C_4$ alkoxy group; A represents a nitrogen atom or a methine group (CH); and Y represents an oxygen atom, a methylene group ($CH_2$), or a methyleneoxy group ($OCH_2$), the method comprising:

(a) reacting a 2-aminonicotinic acid derivative represented by Formula [II]:

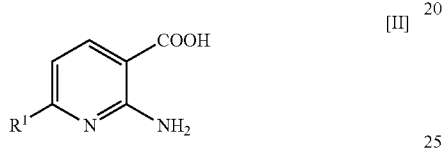

wherein $R^1$ is the same as that defined in Formula [I], with an alkali metal hydride or an alkali metal carbonate to prepare a compound represented by Formula [III]:

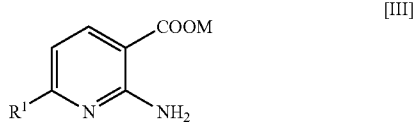

wherein $R^1$ is the same as that defined in Formula [I], and M represents an alkali metal; and (b) reacting the compound represented by Formula [III] prepared in the step (a) with a benzyl halide derivative represented by Formula [IV]:

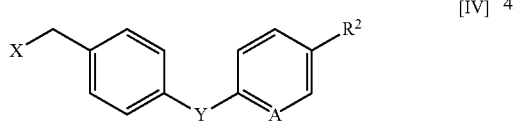

wherein $R^2$, A, and Y are the same as those defined in Formula [I], and X represents a halogen atom, in a polar solvent to produce the 2-aminonicotinic acid benzyl ester derivative represented by Formula [I].

2. The method according to claim 1 comprising:
before the step (b), reacting a benzyl alcohol derivative represented by Formula [V]:

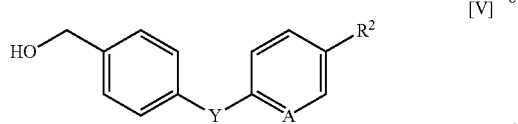

wherein $R^2$, A, and Y are the same as those defined in Formula [I] recited in claim 1, with a halogenating agent to prepare a benzyl halide derivative represented by Formula [IV]:

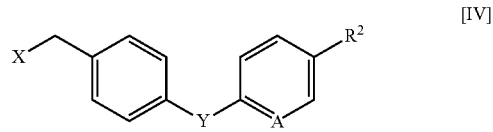

wherein $R^2$, A, and Y are the same as those defined in Formula [I] recited in claim 1, and X represents a halogen atom; and wherein in the step (b), the benzyl halide derivative represented by Formula [IV] thus prepared is reacted, without being isolated, with the compound represented by Formula [III] prepared in the step (a) in a polar solvent to produce the 2-aminonicotinic acid benzyl ester derivative represented by Formula [I].

3. The method of claim 1, wherein the reaction of the compound represented by Formula [III] with the benzyl halide derivative represented by Formula [IV] in the step (b) comprises stirring a mixture thereof with heating at a temperature of from 60° C. to 80° C. for 2 hours to 16 hours.

4. The method of claim 2, wherein the reaction of the compound represented by Formula [III] with the benzyl halide derivative represented by Formula [IV] in the step (b) comprises stirring a mixture thereof with heating at a temperature of from 60° C. to 80° C. for 2 hours to 16 hours.

5. The method of claim 2, wherein the halogenating agent is thionyl chloride, thionyl bromide, or phosphorus oxychloride.

6. The method of claim 4, wherein the halogenating agent is thionyl chloride, thionyl bromide, or phosphorus oxychloride.

7. The method of claim 1, wherein the polar solvent is N,N-dimethylformamide, N,N-dimethylacetamide, N-methylpyrrolidone, 1,3-dimethyl-2-imidazolidinone, acetonitrile, or dimethyl sulfoxide.

8. The method of claim 2, wherein the polar solvent is N,N-dimethylformamide, N,N-dimethylacetamide, N-methylpyrrolidone, 1,3-dimethyl-2-imidazolidinone, acetonitrile, or dimethyl sulfoxide.

9. The method of claim 3, wherein the polar solvent is N,N-dimethylformamide, N,N-dimethylacetamide, N-methylpyrrolidone, 1,3-dimethyl-2-imidazolidinone, acetonitrile, or dimethyl sulfoxide.

10. The method of claim 4, wherein the polar solvent is N,N-dimethylformamide, N,N-dimethylacetamide, N-methylpyrrolidone, 1,3-dimethyl-2-imidazolidinone, acetonitrile, or dimethyl sulfoxide.

11. The method of claim 5, wherein the polar solvent is N,N-dimethylformamide, N,N-dimethylacetamide, N-methylpyrrolidone, 1,3-dimethyl-2-imidazolidinone, acetonitrile, or dimethyl sulfoxide.

12. The method of claim 6, wherein the polar solvent is N,N-dimethylformamide, N,N-dimethylacetamide, N-methylpyrrolidone, 1,3-dimethyl-2-imidazolidinone, acetonitrile, or dimethyl sulfoxide.

* * * * *